United States Patent
Hayashida et al.

(10) Patent No.: US 7,340,034 B2
(45) Date of Patent: Mar. 4, 2008

(54) IMAGE PHOTOGRAPHING APPARATUS AND METHOD

(75) Inventors: Shinsuke Hayashida, Yokohama (JP); Masahiro Tamegai, Ohta-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/531,500

(22) Filed: Sep. 13, 2006

(65) Prior Publication Data

US 2007/0071171 A1 Mar. 29, 2007

(30) Foreign Application Priority Data

Sep. 26, 2005 (JP) ............................. 2005-277804

(51) Int. Cl.
*H05G 1/64* (2006.01)
(52) U.S. Cl. ...................................... 378/98; 378/98.12
(58) Field of Classification Search .................... 378/4, 378/8, 19, 98.9–98.12, 95, 114; 348/247, 348/308; 250/370.09

See application file for complete search history.

(56) References Cited

U.S. PATENT DOCUMENTS

| | | | | |
|---|---|---|---|---|
| 6,084,939 A | * | 7/2000 | Tamura | 378/98.2 |
| 6,298,111 B1 | * | 10/2001 | Ozaki | 378/8 |
| 6,947,084 B2 | | 9/2005 | Kaifu et al. | |
| 7,003,147 B2 | * | 2/2006 | Inoue | 382/132 |
| 2005/0129176 A1 | * | 6/2005 | Kokubun et al. | 378/95 |

* cited by examiner

*Primary Examiner*—Irakli Kiknadze
(74) *Attorney, Agent, or Firm*—Canon USA Inc. IP Division

(57) ABSTRACT

An image processing method generates a small number of still images from a plurality of projected time-series images obtained in time series. The method includes storing the time-series images and performing subtraction between a value of a pixel of an entire or a part of at least one time-series image and a value of a corresponding pixel of an entire or a part of another time-series image. The method further includes detecting the presence or absence of motion by comparing a difference value obtained by performing the subtraction and a threshold value. The stored time-series images are synthesized based on a result of the motion detecting so as to generate a predetermined number of synthesized images.

15 Claims, 8 Drawing Sheets

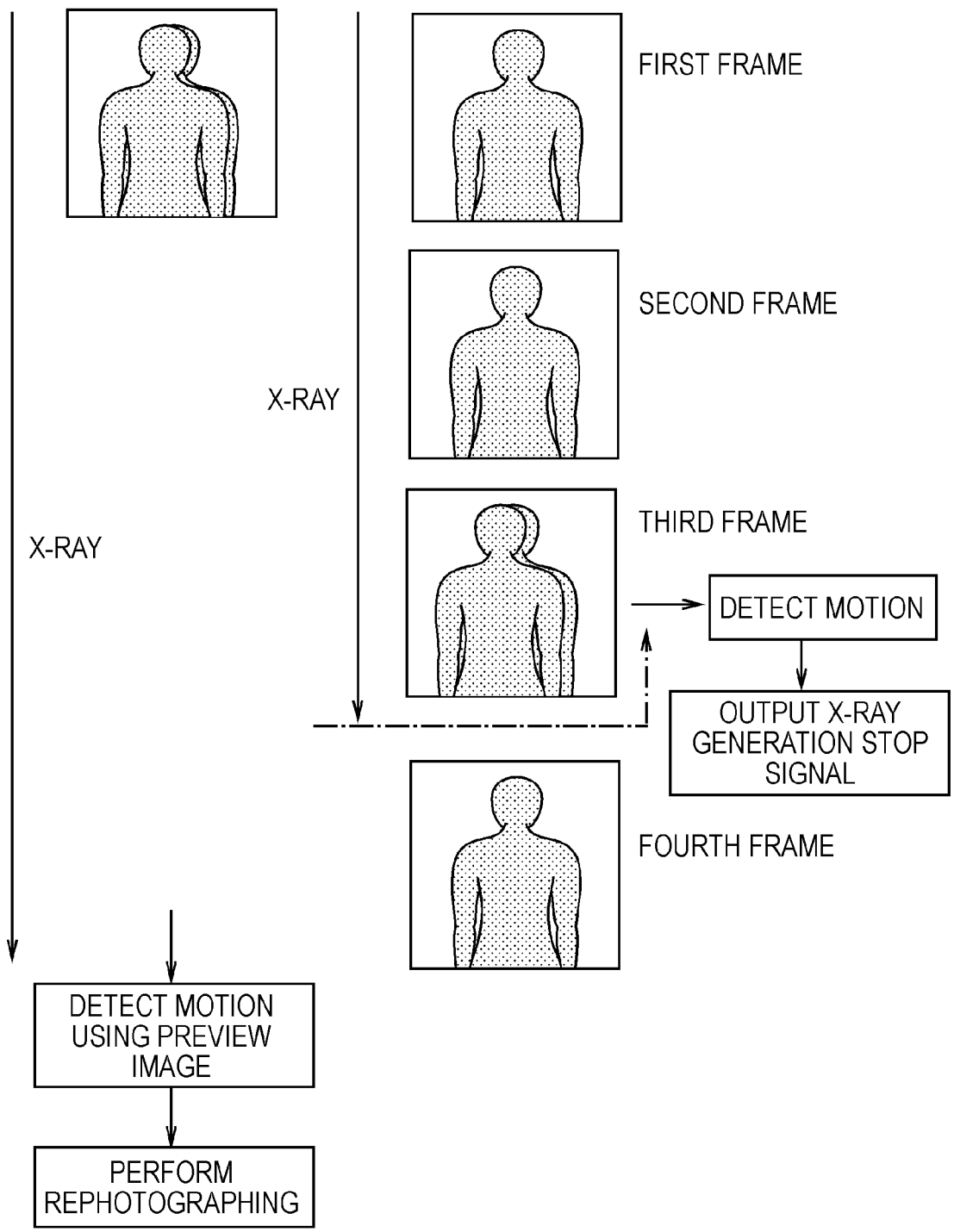

IMAGE PHOTOGRAPHING APPARATUS AND METHOD

BACKGROUND OF THE INVENTION

1. Field of the Invention

The present invention relates to an image photographing apparatus and image photographing method for imaging a distribution of radiation characteristics in an object to be examined which is obtained using an X-ray still image photographing apparatus or the like.

2. Description of the Related Art

X-ray photographing apparatuses have been known in which X-ray beams are emitted from X-ray sources and transmitted through objects to be examined such as medical subjects, and the objects are photographed after the X-ray beams pass through the objects, using screen films, computed radiography (CR) systems, flat panel detectors (FPDs) or the like.

For X-ray photographs, high-resolution solid state X-ray detectors have been developed. Such a solid state x-ray detector has an X-ray sensor in which a two-dimensional array using 500 to 10000 photoelectric conversion devices such as photodiodes are arranged in each dimension. Each photoelectric conversion device generates an electrical signal corresponding to an amount of X-rays incident on the X-ray sensor. An X-ray image is obtained by arranging the object between an X-ray source and the X-ray sensor and converting the amount of X-ray which have been transmitted through the object into an electrical signal. An electric signal from each photoelectric conversion device is read out individually and converted into a digital signal. The digital signal is then processed into an image signal, stored in a recording device, and displayed.

Conventional photographing apparatuses for capturing such X-ray images have been used primarily for still images.

As described in U.S. Pat. No. 6,947,084, for example, a recent photographing apparatus which uses a FPD is capable of reading a plurality of images in a time sequence. Thus, a plurality of images can be output in a still image photographing operation.

A processing procedure of such a still image photographing operation is illustrated in a flowchart shown in FIG. 8. When an X-ray image photographing operation is performed, an object to be examined is positioned between an X-ray generator and a digital X-ray photographing apparatus, at STEP S101. At the same time, a collimator of the X-ray generator is adjusted so that an X-ray beam is irradiated onto an appropriate range and a desired image of the object can be obtained. Thus, the position and range of the incident X-ray beam are determined.

At STEP S102, X-ray photographing is carried out. In STEP S102, an X-ray beam is projected and passes through the object. Then, the X-ray beam is irradiated on the digital x-ray photographing apparatus as an X-ray beam having an intensity distribution and converted into electric charge by a photoelectric conversion device. The electric charge is then converted into a pixel value having an intensity distribution in accordance with the transmissivity of the object. When the irradiation of the X-ray beam is completed, the signal converted by the photoelectric conversion device is read. Then, at STEP S103, a preview of an image representing image data obtained by the digital X-ray photographing apparatus is displayed on a film or a monitor. The preview image obtained in STEP S103 is examined by an operator to manually determine if rephotographing is necessary, at STEP S104. This determining process used to determine the presence or absence of motion or respiration of the object (subject) as well as to determine the presence or absence of a region of interest in the object (subject) is performed in the preview image.

At STEP S105, an image is output which can be used for diagnosing the subject. This image for diagnosis may be a film image or monitor output image. The obtained image is examined and the necessity of rephotographing is determined at STEP S106. When it is determined that rephotographing is not necessary, the processing procedure is terminated, and the subject is freed from the examining position.

As described above, in conventional photographing apparatus which uses an FPD, the necessity of rephotographing or the presence of body motion of a subject is determined by operator's visual observation of photographed image, on the basis of an image output by the photographing apparatus.

However, in such conventional photographing apparatus, the presence or absence of motion of the subject or another factor is determined after a predetermined amount of X-rays are irradiated. Therefore, wasteful operations such as rephotographing cannot be avoided every time when motion is present in a photographed image.

SUMMARY OF THE INVENTION

The present invention has been made in view of this circumstance. The present invention is directed to an image photographing apparatus and method capable of avoiding wasteful operation such as rephotographing and getting a high quality still image.

In an image photographing method according to an exemplary embodiment of the present invention, a small number of still images are generated from a plurality of projected time-series images obtained in time series. This image photographing method includes storing the time-series images, performing subtraction between a value of a pixel of an entire or a part of at least one time-series image and a value of a corresponding pixel of an entire or a part of another time-series image, detecting presence or absence of motion by comparing a difference value obtained by performing the subtraction and a threshold value, and synthesizing the stored time-series images based on a result of the motion detecting so as to generate a number of synthesized images which is smaller than the number of the stored time-series images.

According to an embodiment, the image photographing method further includes performing, during the synthesizing of the stored time-series images, weighting combining on each of the time-series images based on the result of the motion detecting.

According to an exemplary embodiment of the present invention, a radiation image photographing apparatus is provided for generating a small number of still images from a plurality of projected time-series images obtained in time series. The radiation image photographing apparatus includes an X-ray generator, an X-ray generation control device to control generation of X-rays and termination of the generation of X-rays, a two-dimensional sensor to detect X-rays generated from the X-ray generator and output time-series image data, an image memory to store a plurality of pieces of the time-series image data, an image subtraction calculator to calculate a difference value between a value of a pixel of an entire or a part of at least one time-series image and a value of a corresponding pixel of an entire or a part of another time-series image, a motion determinator to determine presence or absence of motion by comparing the difference value calculated by the image subtraction calculator and a threshold value, and an image synthesizing unit to synthesize the stored time-series images based on a result of the motion determinator to generate a number of synthesized images which is smaller than the number of the time-series images.

Other feature and advantage of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principle of the invention.

FIG. 4A and FIG. 4B are diagrams illustrating a difference between an exemplary embodiment and a conventional technique.

DESCRIPTION OF THE EMBODIMENTS

First Exemplary Embodiment

Figure 1:
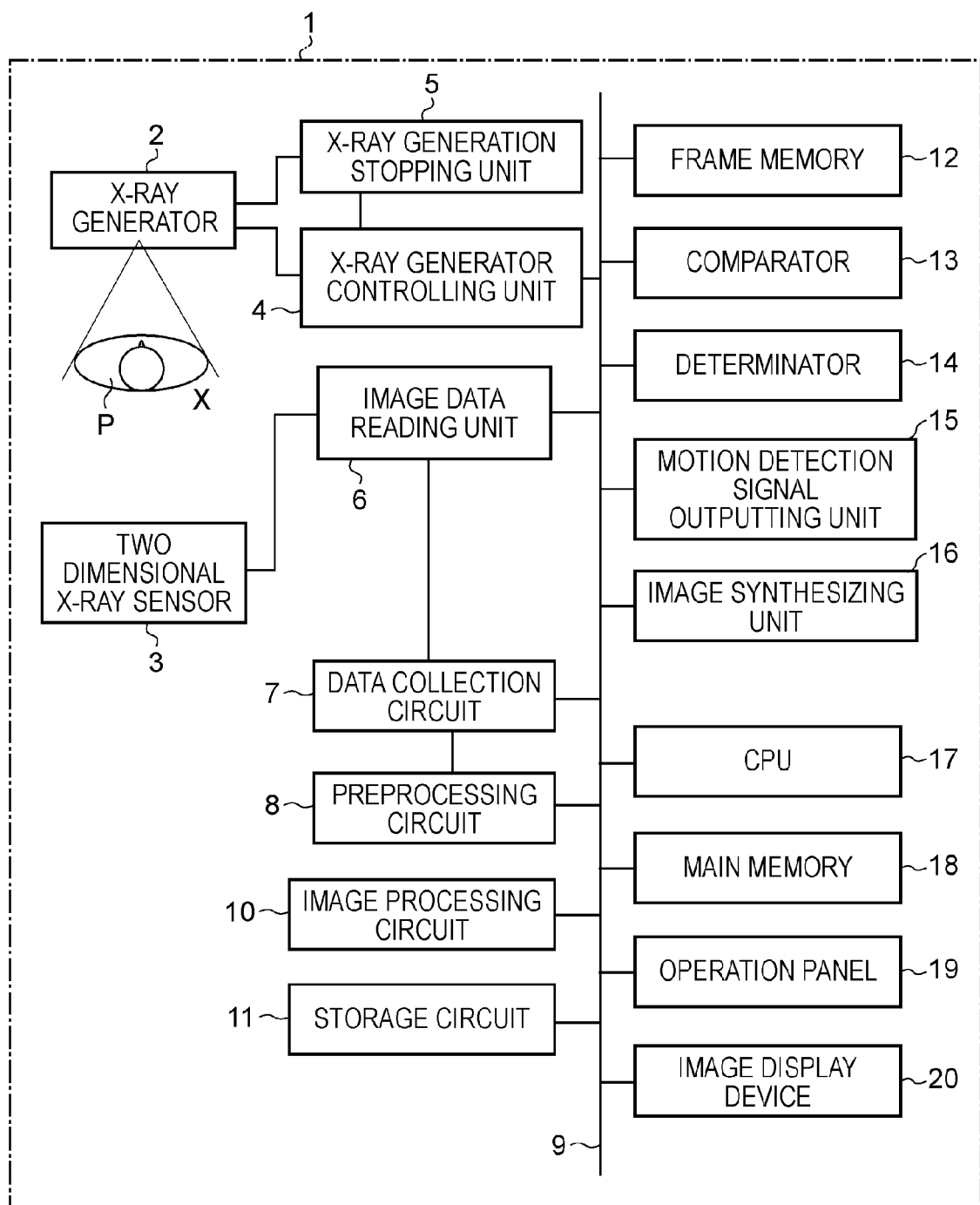
FIG. 1 is a block diagram illustrating an X-ray photographing apparatus according to an exemplary embodiment of the present invention.

FIG. 1 is a block diagram illustrating an X-ray photographing apparatus 1 according to an exemplary embodiment of the present invention. An object to be photographed (subject) P is arranged between an X-ray generator 2 for generating an X-ray beam X and a two-dimensional X-ray sensor 3 for detecting the X-ray beam X. The X-ray generator 2 is connected to an X-ray generator controlling unit 4 directly and via an X-ray generation stopping unit 5. The two-dimensional X-ray sensor 3 is connected to an image data reading unit 6. The image data reading unit 6 is connected to a data collection circuit 7 which is connected to a preprocessing circuit 8.

Each of the X-ray generator controlling unit 4, the image data reading unit 6, the data collection circuit 7, and the preprocessing circuit 8 is connected to a CPU bus 9. The CPU bus 9 is also connected with an image processing circuit 10, a storage circuit 11, a multiple image storing unit (frame memory) 12, a comparator 13, a determinator 14, a motion detection signal outputting unit 15, an image synthesizing unit 16, a CPU 17, a main memory 18, an operation panel 19, and an image display device 20. The main memory 18 stores various data necessary for processing performed in the CPU 17 and also serves as a work memory of the CPU 17. The CPU 17 uses the main memory 18 to perform control of operations of the X-ray photographing apparatus 1 in accordance with an operation instruction inputted by an operator using the operation panel 19.

When a photographing instruction is input by the operator through the operation panel 19, the instruction is transmitted from the CPU 17 to the data collection circuit 7 via the CPU bus 9. Upon receiving the photographing instruction, the data collection circuit 7 controls the X-ray generator 2 and the two-dimensional X-ray sensor 3 through the X-ray generator controlling unit 4 so as to execute an X-ray photographing operation.

In the X-ray photographing operation, the X-ray generator 2 projects an X-ray beam X towards the subject P. The incident X-ray beam X passes through the body of the subject P while attenuating and reaches the two-dimensional X-ray sensor 3. Upon receiving the incident X-ray beam X, the two-dimensional X-ray sensor 3 outputs an X-ray image signal. In this exemplary embodiment, the object P is assumed to be a human body, and thus an X-ray image output form the two-dimensional X-ray sensor 3 is a human body image.

The data collection circuit 7 converts the X-ray image signal output from the two-dimensional X-ray sensor 3 into digital signals and provides the digital signals as primary image data to the preprocessing circuit 8. The preprocessing circuit 8 performs preprocessing such as offset correction processing and gain correction processing on the primary image data provided from the data collection circuit 7, so that secondary image data is obtained. The secondary image data which has undergone the preprocessing is transferred as an original image data to the main memory 18 and the image processing circuit 10 via the CPU bus 9.

The data collection circuit 7 can select a mode for reading image data from the image data reading unit 6, such as a continuous readout mode, a nondestructive readout mode, or other suitable still-image readout mode. A plurality of images which have been consecutively photographed are read by the image data reading unit 6. Then each of the read images is stored in the frame memory 12. The stored images are compared by the comparator 13, and the result of the comparison processing is scored, as will be described in detail below. The determinator 14 performs threshold processing on the obtained processing result to determine whether or not the subject P has moved during the time of image photographing (i.e., whether or not motion of the subject P is present in a frame image). If the determinator 14 determines that motion of the subject P is present in an image, the motion detection signal outputting unit 15 outputs an X-ray generation stop signal so that the irradiation of X-rays is discontinued. Upon receiving the X-ray generation stop signal, the X-ray generator controlling unit 4 causes the X-ray generation stopping unit 5 to stop the generation of X-rays from the X-ray generator 2.

Figure 2:
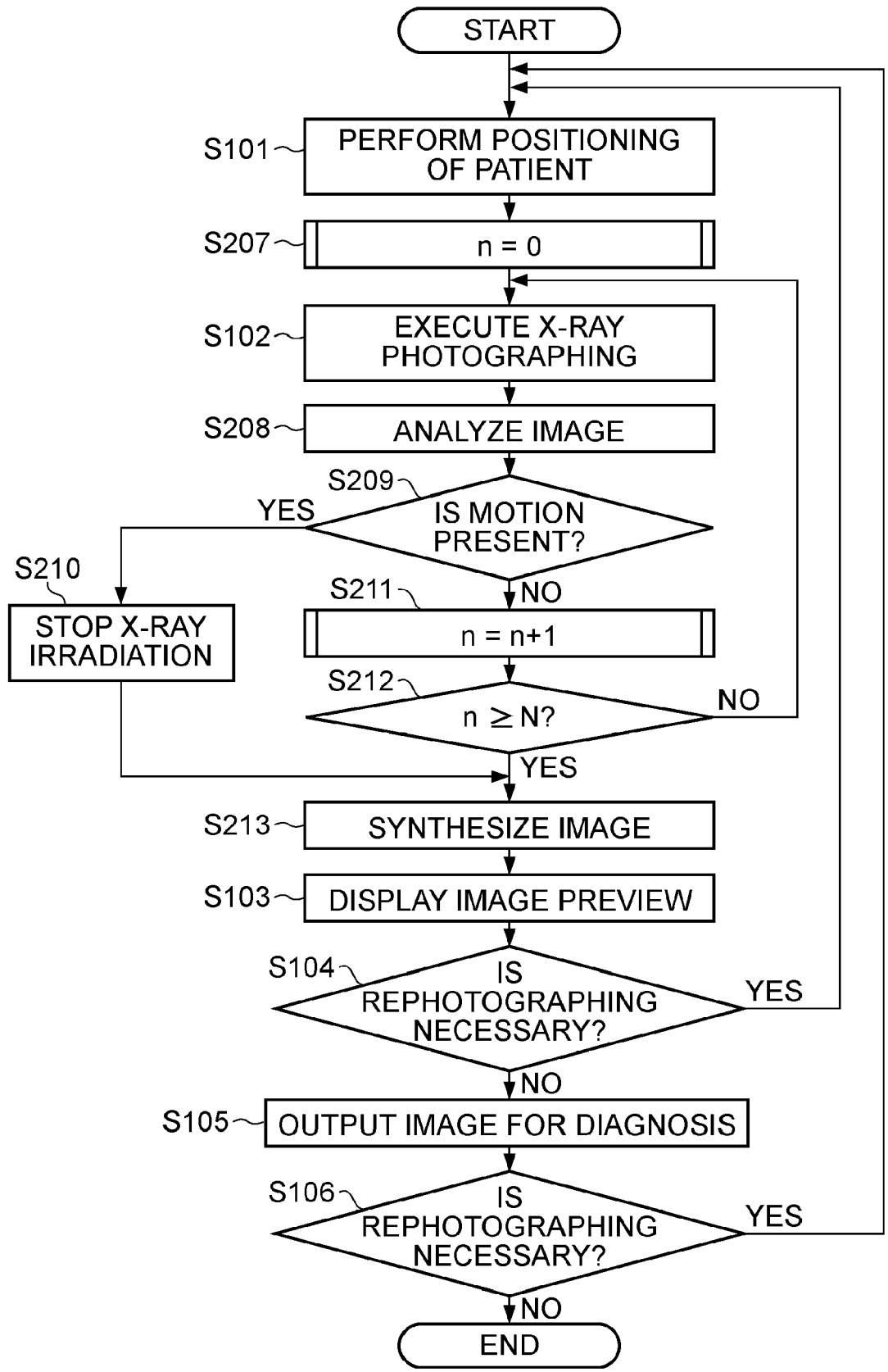
FIG. 2 is a flowchart illustrating a radiation image processing according to a first embodiment of the present invention.

A processing procedure according to a first exemplary embodiment is illustrated in a flowchart shown in FIG. 2. For simplicity of description, the same reference numerals are used to designate generally the same processing steps illustrated in FIG. 2 and FIG. 8 which illustrates a processing procedure performed in a conventional technique. Processing steps which are similarly performed in both the processing procedure of this exemplary embodiment and the conventional processing procedure are STEP S101, STEP S102, and STEP S103 to STEP S106. In the first exemplary embodiment, between the processing of STEP S102 and STEP S103, processing of STEP S208 and STEP S209 for detecting the presence or absence of motion of the subject P and STEP S210 for stopping X-ray generation are performed. In addition, in the processing procedure of the first embodiment includes processing of STEP S211 to STEP S213 so that images in each of which a small amount of motion of the subject P is present are synthesized. With this arrangement, wasteful photographing operations can be minimized and an exposure dose to the subject P can be reduced.

In the first exemplary embodiment, electric signals are read which have been sequentially converted by a photoelectric conversion device while X-rays are being irradiated, at STEP S102. Since the image data reading unit 6 employs either a continuous video image readout (pulse video image readout) mode or a nondestructive readout mode, the presence or absence of motion can be determined before the irradiation of X-rays is completed. It can be configured such that the processing of STEP S103 for displaying an image preview is performed before the processing of STEP S208 for image analysis. However, performing the motion determination processing after the preview image is displayed results in unnecessary X-ray exposure to the subject P after motion of the subject occurs. Thus, in this exemplary embodiment, the motion determination processing is performed between STEP S102 and STEP S103. This arrangement permits automatic determination of the presence or absence of motion in an earlier stage of a photographing operation.

Firstly, at STEP S101, positioning of the subject P is performed. Then, at STEP S207, a value representing the number n of images to be photographed is initialized. Although X-ray images are photographed as still images while the X-ray beam X is irradiated in STEP S102, they are stored in the frame memory 12. As means for storing a plurality of images, either one of the continuous readout mode or the nondestructive readout mode is employed, which is selected in the image data reading unit 6. The X-ray images photographed by the two-dimensional X-ray sensor 3 are sequentially stored in the frame memory 12.

In the conventional technique, a photographed image is processed before the image is output to an image display device. In contrast, in this exemplary embodiment, images is not required to undergo processing through the preprocessing circuit 8 and the image processing circuit 10 before the determination of the presence or the absence of motion of the subject P is performed. Needless to say, if the images are processed using these circuits before the motion determination, the quality of the image is enhanced, and thus the motion determination processing can be performed with increased precision. Therefore, when the CPU 17 or the main memory 18 has a sufficient calculation capacity, it is desirable to process the images through these circuits before the motion determination processing is performed. However, when the two-dimensional X-ray sensor 3 produces stable output and sufficient calculation capability is unavailable, it is desirable not to process the images through these circuits in an effort to increase processing speed.

Subsequently, at STEP S208, the X-ray images photographed in STEP S102 are read from the frame memory 12 so as to be analyzed, which will be described in more detail below. Then, at STEP S209, the presence or absence of motion of the subject P in each image is determined. In this motion determination processing, it is desirable that threshold processing is performed for determining the presence or absence of motion by using not only a result of comparison processing performed between the frame images, but also information, such as information on a photographed region (e.g., whether or not the heart of the subject P is present in the images) and position information of a lesion such as a tumor, which will be described below.

If, in STEP S209, it is determined that motion of the subject P is present, the X-ray irradiation is stopped, at STEP S210. A signal output from the motion detection signal outputting unit 15 causes the X-ray generator controlling unit 4 to output an X-ray generation stop signal to the X-ray generation stopping unit 5 so that the generation of X-rays from the X-ray generator 2 is stopped. Alternatively, in a case where an irradiation period is controlled using a phototimer for controlling the amount of X-rays, an X-ray stop signal output from the phototimer can preferentially be applied for stopping the loop.

If, in STEP S209, it is determined that no motion of the subject P is present, the processing procedure proceeds to STEP S211. Then, in STEP S212, the processing of STEP S102 to S212 is repeated until the number of photographed images reaches a predetermined number N which is set using, for example, the operation panel 19.

At STEP S213, the images obtained through the procedure from STEP S101 to STEP S211 are synthesized. The number of synthesized images is less than the number of images obtained by the image data reading unit 6. When a still image is desired as in the conventional technique, the number of synthesized images is one. From the viewpoint of image synthesis, it is desirable that all frame images have the same storage time and frame rate. This is because the amount of dark current in an FPD is dependent on storage time. Thus, a stable image can be obtained by storing the images synchronously.

The image synthesis processing is desirably performed by simple addition, if it is determined in STEP S209 that no motion of the subject P is present. However, if it is determined in STEP S209 that motion of the subject P is present, weighting addition is desirably employed for image synthesis, in which a small weight is assigned to a frame image in which motion of the subject P is determined to be present. In addition, an addition technique can be employed in which zero weighting is assigned to such a frame image in which motion of the subject P is determined to be present.

Figure 8:
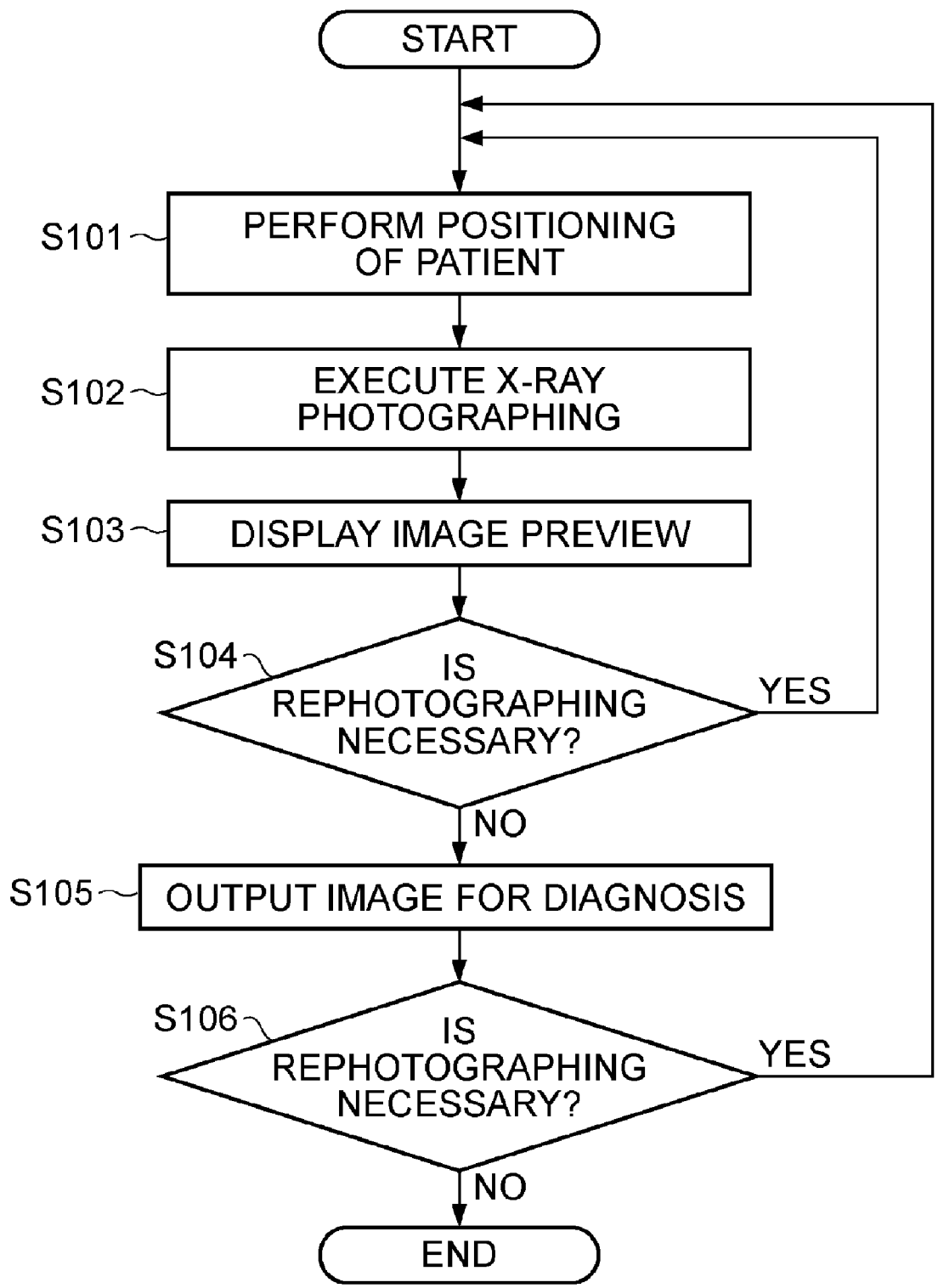
FIG. 8 is a flowchart illustrating a convention radiation image processing.

Processing of STEP S103 and thereafter is performed in the same order as that in which the processing of STEP S103 to STEP S106 is performed in the conventional technique, which is described with reference to FIG. 8. However, the processing order of the image synthesis processing of STEP S213 and the preview image display processing of STEP S103 can be inverted. This is because displaying a single frame image before image synthesis allows the operator to check whether or not the irradiation field and the position of the subject P are appropriately arranged. Thus, in this exemplary embodiment, part of the purpose of the image preview display can be achieved even if the order is inverted as described above. The preview image displayed in STEP S103 is not necessarily an image created at full radiation dose.

An advantage associated with altering the processing order as described above is that earlier display of image preview can shorten the entire photographing cycle. On the other hand, with this altered processing order, the presence or absence of body motion or respiratory motion of the subject P cannot be detected with sufficient precision in the subsequent STEP S104. In this case, whether or not rephotographing is necessary is determined using another parameter. Thus, the presence or absence of body motion or respiratory motion of the subject P is determined after an image for diagnosis is output at STEP S105, and the necessity of rephotographing is determined at STEP S106.

If it is determined that rephotographing is not necessary in STEP S104 performed subsequent to STEP S103, an image for diagnosis is output, at STEP S105. If, in STEP S106, it is determined that rephotographing is not necessary, the processing procedure is terminated.

Figure 3:
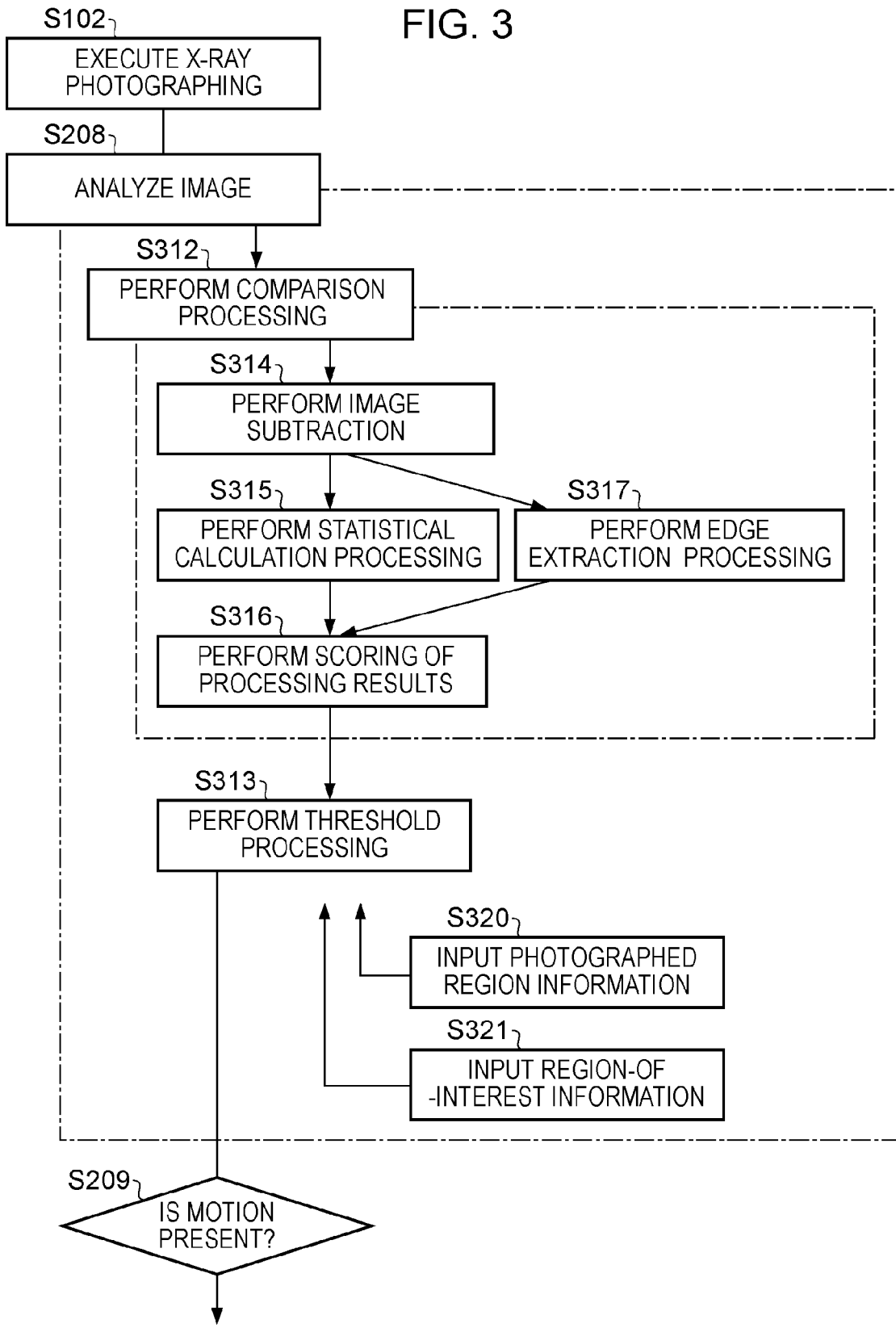
FIG. 3 is a flowchart illustrating an image analysis operation according to an embodiment of the present invention.

FIG. 3 is a flowchart specifically illustrating the image analysis processing of STEP S208 of FIG. 2 for detecting body motion of the subject P. The processing to be performed before and after the processing of STEP S208 is described with reference to FIG. 2, and therefore a description thereof will be omitted. This image analysis processing generally includes comparison processing (STEP S312) and threshold processing (STEP S313) which are performed in that order.

The comparison processing of STEP S312 includes image subtraction processing (STEP S314), statistical processing (STEP S315) and processing result scoring processing (STEP S316). Firstly, at STEP S314, subtraction is performed between the pixel values of the frame images on a pixel to pixel basis so that a difference images is obtained. Then, in the statistical processing of STEP S315, the difference image is analyzed.

In the statistical processing of STEP S315, a standard deviation and a mean value of the difference image are calculated for each region or each image area. The purpose of this processing of STEP S315 is to detect the presence or absence of motion of the subject P, and therefore the simplest standard deviation calculation can be applied. The subtraction between two adjacent frame images produces a range of standard deviation which is wider than that is specified, if body motion or respiratory motion of the subject P is present. Such a simple statistical processing can be performed in a short time and is thus advantageous when the output of the X-ray generator 2 is stopped during a photographing operation.

On the other hand, when the output of the X-ray generator 2 is not stopped, i.e., the generation of X-rays does not need to be stopped, a longer calculation time is applied. Such a longer calculation time is advantageous in that it increase precision of determination processing performed in a subsequent processing step. This longer calculation time is preferred in a case where it is desired to precisely verify the presence or absence of body motion of the subject P after an X-ray exposure sequence ends.

One of the schemes which can be employed to increase the calculation time is edge extraction processing (STEP S317). When motion of the subject P is present, each pixel value of the difference image is inverted, and usually a discontinuous edge appears in the difference image. In this edge extraction processing of STEP S317, the presence or absence of such a discontinuous edge is determined. This results in higher precision in the motion determination processing as compared with the case in which the statistical processing is performed.

The edge extraction processing will be advantageous if capabilities of the CPU 17 and the main memory 18 are enhanced or algorithm execution speed in the edge extraction processing is increased in the future. The results of statistical processing or the edge extraction processing performed multiple times are scored and the scores are weighted. In addition, a large weight for scoring is applied to a value which markedly depends on the presence or absence of body motion or respiratory motion. A case where the body of the subject P is very thick, which hinders X-rays from passing through the subject P, should be specifically considered. In such a case a very small amount of X-rays reaches the two-dimensional X-ray sensor 3 resulting in a large standard deviation value of difference images due to X-ray quantum noise. Consequently, the standard deviation value becomes closer to a threshold value with which body motion or respiratory motion of the subject P is determined to be present. In this case, the edge extraction processing can assist the motion determination processing.

In this case, for example, it is desirable that the result of the statistical processing and the result of the edge extraction processing are multiplied, and then the scoring processing is performed on the multiplied result at STEP S316. At this time, when the result of the edge extraction processing is 0, the result of the multiplication is also 0 regardless of the value obtained as the result of the statistical processing. Thus, even if a large value is obtained as the result of the statistical processing, it is determined that no body motion or respiratory motion of the subject P is present.

The purpose of the comparison processing of STEP S312 is to detect the presence or absence of body motion or respiratory motion of the subject P in the multiple images. Therefore, for simplicity of the image comparison processing, it is desirably configured such that images to be compared which have been read in the preceding processing step have the same storage time and frame rate, and then subtraction is performed on two adjacent frame images. Alternatively, it is also desirable that the first frame image is set as the reference image used for subtraction performed on the rest of the frame images. The use of such a reference image is advantageous in motion detection processing when large-scale and slow motion of subject P is present.

In STEP S316, which is associated with the comparison processing (STEP S312), the processing results are scored. Then, in the threshold processing (STEP S313), the presence or absence of body motion or respiratory motion of the subject P is determined by determining whether or not each of the scores is greater than a predetermined threshold value. This determination operation desirably includes a process of inputting photographed region information (STEP S320) which indicates, for example, whether or not an image of the heart of the subject P is present in photographed images, and a process of inputting information on a region of interest (STEP S321) which is indicative of the position of a lesion such as a tumor. It is noted that a statistical value obtained in the statistical processing including an exposure dose markedly depends on whether the region of interest is a bone or a lung field. Therefore, the threshold value used in the threshold processing can be appropriately selected in accordance with the photographed region information and the region of interest information.

FIGS. 4A and 4B illustrates a difference between a conventional technique and a technique according to this exemplary embodiment in a photographing procedure. FIG. 4A illustrates the conventional technique, and FIG. 4B illustrates this exemplary embodiment. In this example, a case is illustrated where the subject P moves to the right while facing toward the X-ray generator 2 during an X-ray photographing operation. If the subject P does not move while four images (a first frame image to a fourth frame image) are sequentially captured during the photographing operation, one still image can be obtained by adding the four frame images.

However, as illustrated in FIG. 4B, motion of the subject P is present in the third frame image. In such a case, the third frame image and the first or second frame image are compared in the comparison processing of STEP S312, and it is determined that body motion of the subject P is present on the basis of an output value obtained in the threshold processing of STEP S313. The motion detection signal outputting unit 15 outputs a signal in accordance with the determination result. In response to this signal, the X-ray generator controlling unit 4 provides an X-ray generation stop signal to the X-ray generation stopping unit 5. Thus, the irradiation of the X-ray beam X is stopped before the fourth frame image is photographed.

If the conventional technique illustrated in FIG. 4A is used in the above case, X-rays are irradiated for a predetermined time period. As a result, a blurring image associated with the motion of the subject P is output. Consequently, for example, rephotographing is performed, resulting in an increased exposure dose to the subject P, a reduced throughput for a photographing operation, and an increased burden on the subject P.

On the other hand, in the technique according this exemplary embodiment, an image in which no body motion of the subject P is present by synthesizing images obtained before the motion of the subject P occurs. With this arrangement, the possibility that rephotographing is required. In addition, since the generation of X-rays is stopped when the motion of the subject P occurs, the exposure dose to the subject P can be reduced.

Second Exemplary Embodiment

Figure 5A:
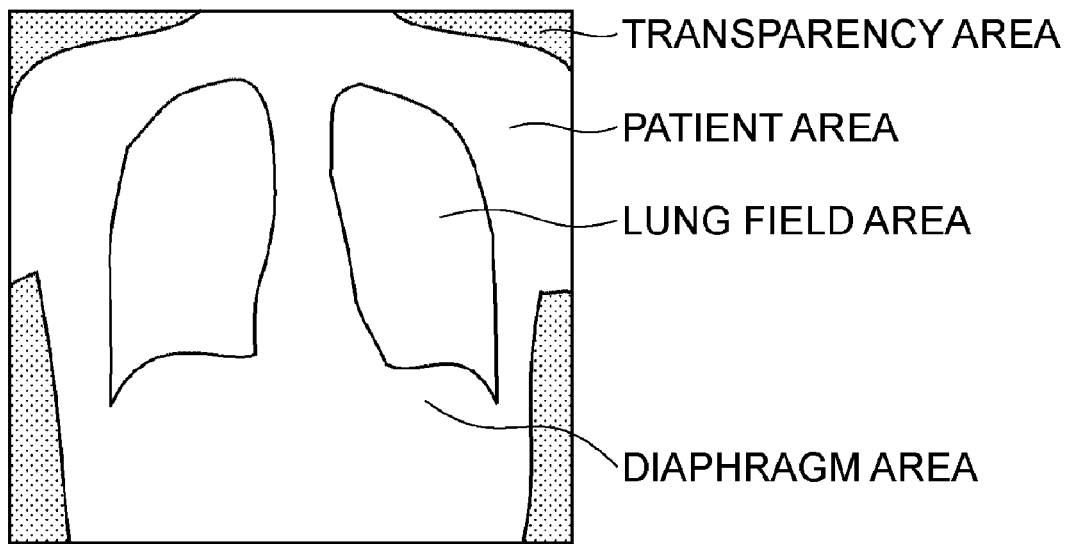
FIG. 5A and FIG. 5B are diagrams illustrating motion of a front chest during a respiratory cycle.
Figure 5B:
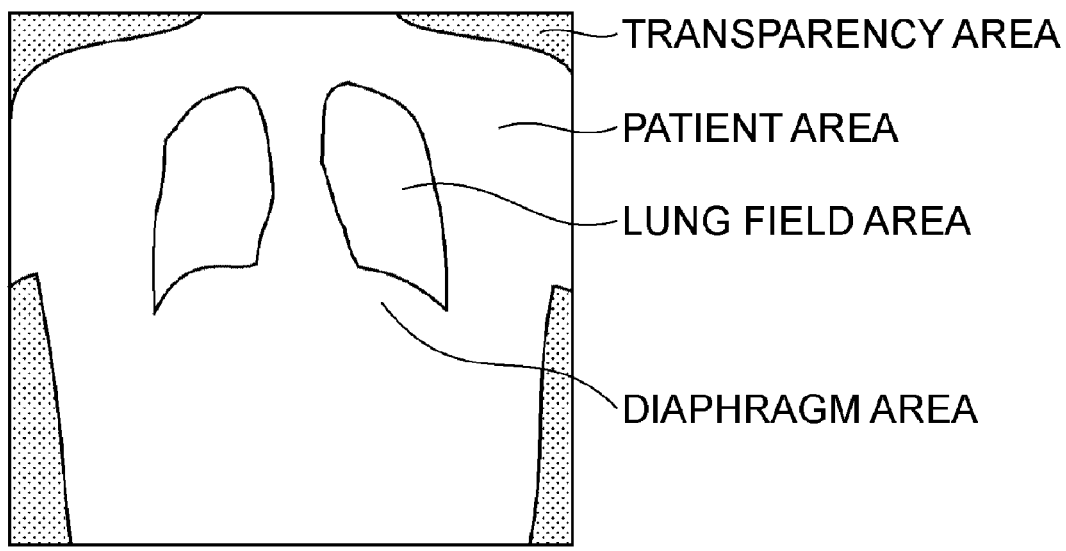

FIG. 5A and FIG. 5B show the front chest image illustrating motion which takes place when the subject breathes. FIG. 5A illustrates a case where a photographing operation is performed in which the subject P deeply inhales and holds his or her breath in accordance with operator's instruction. FIG. 5B represents an image obtained when motion occurs which is associated with normal breathing of the subject P. The operator gives the subject P an instruction by saying, "Breathe in deeply, and hold your breath" before obtaining an image, thereby requesting the subject P to stop the respiratory motion of the lung as well as the body motion.

However, there may be a case where the subject P fails to hear the instruction or stop his or her motion as instructed. There may also be a case where the subject P breathes, which causes the motion of the lung during the photographing operation. In this case, normally, the diaphragm moves upward making the lung field smaller during exhale, as illustrated in FIG. 5B.

Thus, as described above, there are several types of body motion depending on the causes, and cases may often occur where not the entire subject moves but a part of the subject P moves. For example, when the subject P breathes, the amount of motion which takes place around the upper lung field is small. On the other hand, breathing of the subject P causes a large amount of regional change in the vicinity of the diaphragm, as illustrated in FIGS. 5A and 5B. For an image area having no regional change, all of the frame images can be added. In a second exemplary embodiment, for an image area in which a very large amount of regional change is present, weighting addition is performed by applying a small weight to a frame image captured at a time when the amount of regional change is large. Thus, synthesizing schemes can be altered in accordance with image areas, so that a synthesized image can be produced with a small exposure dose.

Figure 6:
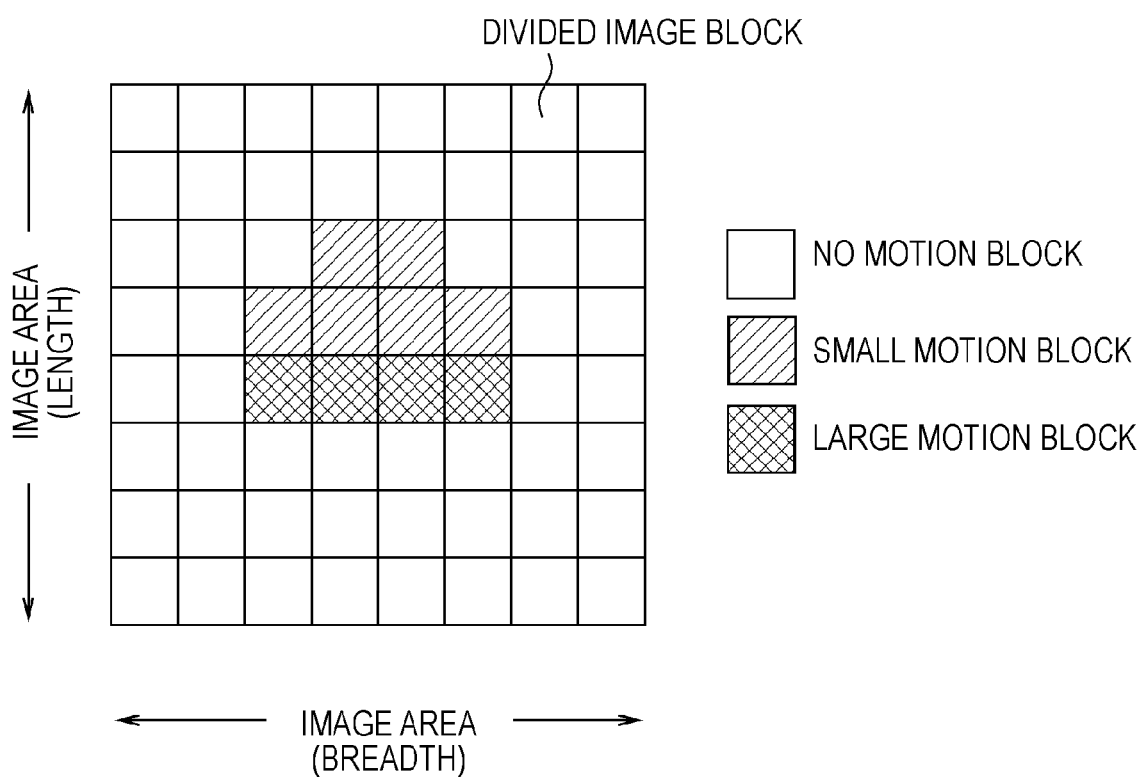
FIG. 6 is a schematic diagram illustrating a result of a motion calculation for each image block according to an exemplary embodiment of the present invention.

FIG. 6 is a schematic diagram illustrating a result of a motion calculation. In this motion calculation, an image is divided into small image blocks and the presence or absence of a regional change is detected for each of the image blocks. In the second exemplary embodiment, an amount of regional change is calculated for each of the image blocks. Then, an amount of a weight to be applied in weighting addition for each frame image is determined for each of the image blocks. In this exemplary embodiment, the case is described where the image blocks are square as shown in FIG. 6. However, the shapes of the blocks are not limited to square, and the shapes and sizes of the images blocks can be selected after irradiation field recognition, region recognition, and organ recognition are performed by the image processing circuit 10. In this case, it is desirable that an image block representing part of an organ having a large amount of regional change is extracted, and an amount of weight is applied to those extracted image blocks which is different from that applied to image blocks representing another image area in which no regional change is present.

Figure 7:
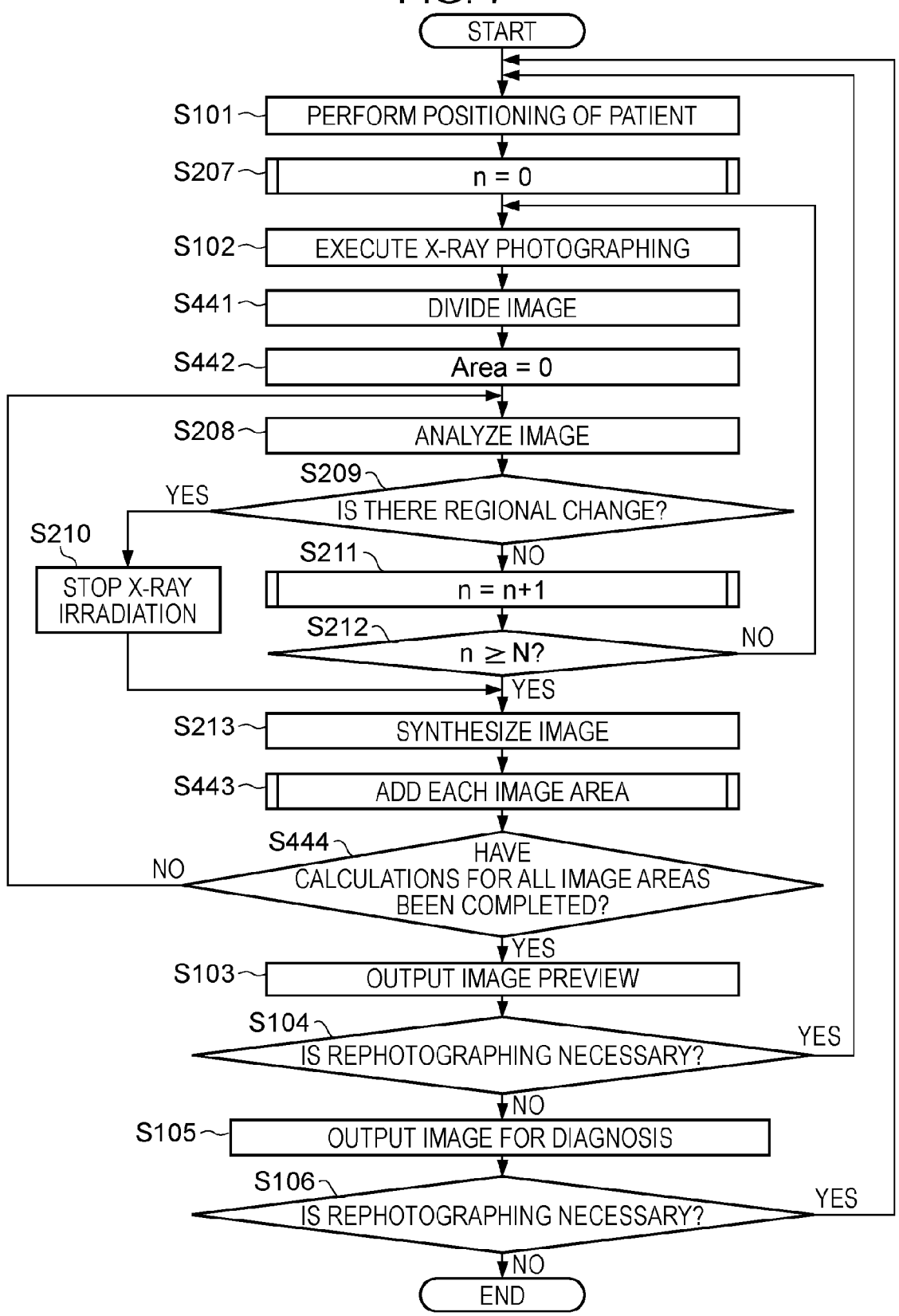
FIG. 7 is a flowchart illustrating a radiation image processing according to a second embodiment of the present invention.

Referring now to FIG. 7, a flowchart illustrates a processing procedure according to the second exemplary embodiment. The processing steps which are the same as those in FIG. 2 are designated by the same reference numerals as in FIG. 2. This processing procedure is different from that described in the first exemplary embodiment in that each image is divided into image blocks, and thus STEP S441 to STEP S444 are performed in addition to the processing procedure described in FIG. 2. In STEP S441 through STEP S443, image division processing and determination of the presence or absence or an amount regional change in each of the image blocks are performed.

At STEP S441, the image processing circuit 10 divides a photographed image into small image blocks, as described with reference to FIG. 6. Then, in STEP S442 through STEP S444, the following processing procedure is repeated so that the amount of regional change in every image block can be obtained. At STEP S208, image analysis is performed for each block, and frame images are compared on a block by block basis for each of time points at which the individual frame images are captured, so that the presence or absence of regional change and, if present, the time point at which the regional change occurs are calculated.

Subsequently, at STEP S209, the presence or absence of regional change is determined for each image block in the individual each image areas. If it is determined that a regional change is present, processing for stopping the irradiation of X-rays is performed at STEP S210. Then, frame images which have been obtained until then are synthesized by applying a relatively large weight to each frame image in which no regional change is present.

A criterion for stopping X-ray irradiation in STEP S210 after the determination of the presence or absence of regional change is performed in STEP S209 is different from that used in the case of the first exemplary embodiment which is illustrated with reference to FIG. 2. In this embodiment, information of each image area is considered. Specifically, when large motion is present in an image area, there are three possible cases to be considered: (i) the range of the regional change is small; (ii) the amount of the regional change is small; (iii) the region of the regional change is largely different from the region of interest. In these cases, a threshold value, which is used in the threshold processing of STEP S313 performed for determining the presence or absence of a regional change in STEP S209, is adjusted so that the X-ray generator controlling unit 4 will not output an X-ray generation stop signal to the X-ray generation stopping unit 5. In this exemplary embodiment, unlike the conventional technique, two pieces of information associated with (i) and (iii) described above are considered.

In order to determine whether or not the processing procedure according to this exemplary embodiment is performed, the following factors have to be considered: (a) the processing capability of the components (CPU 17, main memory 18, CPU bus 19) which perform the image analysis processing of STEP S208; (b) whether or not means for stopping X-ray generation is implemented. In regard to the factor (a), it is possible to enhance the processing capability by modifying an algorithm or by load decentralization. When these components have sufficient processing speed, the processing procedure of the second exemplary embodiment is more advantageous as compared with the first exemplary embodiment. However, when the components do not have sufficient processing speed, not only the factor (a) but also the factor (b) are considered. Specifically, when the X-ray beam X is to be stopped, a fast operation processing is preferred in view of determining whether or not X-ray generation is stopped. Therefore, in this case, the processing procedure of the first exemplary embodiment is preferred.

TABLE 1 shows general effects of the first and second embodiments.

TABLE 1

| | Photographing mode | Readout mode | Timing of motion detection |
|---|---|---|---|
| Conventional technique | still image photography | still image readout | on image preview after photographing |
| Embodiment 1, 2 | still image photography | video image readout | motion occurrence time + calculation time |
| Embodiment 1, 2 | still image photography | nondestructive readout | motion occurrence time + calculation time |

In those photographing techniques which use FPDs, the photographing techniques according to the present exemplary embodiments are generally the same as the conventional technique in the photographing mode (still image photography). However, as described above, it is possible, in the present exemplary embodiments, to read images in a video image readout mode or a nondestructive readout mode. Then, the read images can be synthesized in accordance with storage time so that a still image is created. This technique, in combination with the processing of the second exemplary embodiment, permits earlier determining timing of motion of an object, as described above.

In the conventional technique, determination of the presence or absence of body motion is performed when a preview image is output. On the other hand, in the second exemplary embodiment, the presence or absence of a regional change can be determined as soon as calculations for image analysis are completed which are performed immediately after the regional change occurs.

Thus, an earlier timing of regional change determination is achieved by the processing of the second exemplary embodiment, and consequently reduction of exposure dose and increased efficiency of throughput can also be achieved. A reduced exposure dose can be achieved by stopping irradiation of X-rays when the presence of a regional change is detected. In the conventional technique, by observing a preview image (or a film output image), it is determined whether or not a photographing operation has been carried out as expected (including the presence or absence of regional change). On the other hand, in the second exemplary embodiment, if a regional change occurs, the regional change can be recognized using calculators before an image preview is output. Thus, the presence of the regional change in an image can be detected faster than the conventional technique, which brings about an increased efficiency of throughput.

In addition, as a secondary effect of the present exemplary embodiments, the necessity of rephotographing can be reduced. Normally, rephotographing is required when an image is obtained in which motion of a subject is already present. Therefore, rephotographing doubles a necessary exposure dose when performed under the same photographing condition as that applied in the first-time photographing operation.

On the other hand, in the second exemplary embodiment, when a regional change occurs at a later stage of a photographing sequence, there may be a case where images which have been captured until the regional change occurs are enough to create a synthesized image that meets requirement for use in diagnosis. In such a case, in determining whether or not rephotographing is carried out, advantages and disadvantages associated with rephotographing are considered. Rephotographing has an advantage in that more information is provided to an operator. On the other hand, performing rephotographing is disadvantageous in that an exposure dose against a subject is increased and that the subject has to wait longer for another photographing operation.

In the above case, rephotographing is determined to be unnecessary in some circumstances. For example, a case can be assumed where, in an X-ray photographing operation with an irradiation period of 50 ms, a subject holds his or her breath for the first 90 percent of the irradiation period (i.e., 45 ms) but breaths for the last 10 percent (i.e., 5 ms). In this circumstance, when the photographing operation is performed at 200 frames/s, normally, ten frame images are added together so that a still image is formed, and only the last frame image shows the presence of motion around the lung field area.

In such a circumstance, in the conventional photographing technique, rephotographing cannot be avoided since a regional change is present in an output image due to the respiratory motion of the subject which occurs in the last 5 ms of the photographing operation. On the other hand, in the second exemplary embodiment, frame images obtained during the first 45 ms in which no regional change is present are used for creating a synthesized image. Thus, even if a regional change occurs during a photographing sequence, rephotographing does not need to be performed as long as images have been obtained which are enough to meet requirements for diagnosis. This consequently brings about the effects of reducing exposure dose and increasing efficiency of throughput.

In the second exemplary embodiment, the case is described in which the lung field of the subject P largely moves. In addition to this lung motion, inside a human body, there are tissues such as blood which always circulate and organs such as the heart which always moves. The motion of such tissues and organs cannot be stopped with the intention of the subject P. Therefore, in the threshold processing of STEP S313 and region information input of STEP S320 as illustrated in FIG. 3, adjustment is performed so that the motion of such tissues and organs are not detected.

In STEP S213 of FIG. 7, when images are synthesized, an amount of weight applied for the weighting addition performed on frame images is adjusted for each of the image areas. This processing is repeated in STEP S443 for each image area. Then, at STEP S444, if it is determined that calculations for all image areas have been completed, the calculation processing is terminated. However, in the processing of STEP S444, calculations are not necessarily performed for all image areas, which is not illustrated in FIG. 7. For example, a result obtained by an irradiation field recognition circuit in the image processing circuit 10 can be used for the calculation processing. Thus, by limiting the image areas on which the calculation processing is performed, the calculation speed can be increased.

Further, this the present invention can also be achieved by providing a system or apparatus with a storage medium that stores a program code of software for realizing the functions of the above-described embodiment, and causing a computer (or a CPU, MPU or the like) of the system or apparatus to read the program code from the storage medium and then to execute the program code. In this case, the program code itself read from the storage medium realizes the functions of the embodiment described above, and a storage medium storing the program code constitutes the invention.

In addition, the storage medium for providing the program code includes a flexible disk, a hard disk, an optical disk, a magneto-optical disk, a CD-ROM, a CD-R, a CD-RW, a DVD-ROM, a DVD-RAM, a DVD-RW, a DVD-R, a magnetic tape, a non-volatile memory card, a ROM, etc.

Furthermore, besides the program code read by the computer being executed to realize the functions of the above-described embodiment, the present invention includes an OS (operating system) or the like running on the computer performing an actual process in whole or in part according to instructions of the program code to realize the functions of the above-described embodiment.

Moreover, the present invention also includes a CPU or the like contained in a function expansion board inserted into the computer or in a function expansion unit connected to the computer, the function expansion board or the function expansion unit having a memory in which the program code read from the storage medium is written, the CPU or the like performing an actual process in whole or in part according to instructions of the program code to realize the functions of the above-described embodiment.

As many apparently widely different embodiments of the present invention can be made without departing from the spirit and scope thereof, it is to be understood that the invention is not limited to the specific embodiment thereof except as defined in the claims.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2005-277804 filed on Sep. 26, 2005, which is hereby incorporated by reference herein in its entirety.

What is claimed is:

1. A method in which a still image is generated from a plurality of projected time-series images obtained in time series, the method comprising:
    storing the time-series images;
    calculating a difference value between a value of a pixel of an entire or a part of at least one time-series image and a value of a corresponding pixel of an entire or a part of another time-series image;
    detecting presence or absence of motion by comparing the difference value and a threshold value; and
    synthesizing the stored time-series images based on a result of the motion detecting so as to generate a synthesized still image.

2. The method of claim 1, further comprising generating an X-ray generation stop signal based on the result of the motion detecting.

3. The method of claim 1, further comprising performing, in the image synthesizing, weighting synthesis on each of the time-series images based on the result of the motion detecting.

4. The method of claim 3,
    wherein, in the weighting synthesis, a weight is applied to each of the stored time-series images in accordance with each time frame.

5. The method of claim 1, further comprising dividing each of the time-series images into a plurality of image blocks.

6. The method of claim 5, further comprising applying a weight to each of the image blocks based on a result obtained by the calculating,
    wherein each image area is weighted based on the block weighting so that the image synthesizing is executed.

7. A radiation image photographing apparatus for generating a still image from a plurality of projected time-series images obtained in time series, the apparatus comprising:
    an X-ray generator;
    an X-ray generation control device to control generation of X-rays and termination of the generation of X-rays;
    a two-dimensional sensor to detect X-rays generated from the X-ray generator and output time-series image data;
    an image memory to store a plurality of pieces of the time-series image data;
    an image subtraction calculator to calculate a difference value between a value of a pixel of an entire or a part of at least one time-series image and a value of a corresponding pixel of an entire or a part of another time-series image;
    a motion determinator to determine presence or absence of motion by comparing the difference value calculated by the image subtraction calculator and a threshold value; and
    an image synthesizing unit to synthesize the stored time-series images based on a result of the motion determinator to generate a synthesized still image.

8. The apparatus of claim 7, further comprising
    a motion detection signal outputting unit to generate an X-ray generation stop signal based on the result of the motion determinator.

9. A method comprising:
    irradiating an X-ray towards an object to be examined;
    detecting an X-ray passing through the object and generating X-ray image signals;
    generating a plurality of time-series images based on the X-ray image signals;
    comparing values of pixels of at least a portion of one of the time-series images and values of corresponding pixels of another one of the time-series images and generating a comparison value;
    detecting if motion is present in the time-series images based on the comparison value; and
    synthesizing the time-series images based on a result of the motion detecting to generate a synthesized still image.

10. The method of claim 9, further comprising
    dividing each of the time-series images into a plurality of image blocks.

11. The method of claim 10,
    wherein the motion detecting is performed on each respective one of the image blocks.

12. The method of claim 11, further comprising
stopping the irradiation of the X-ray if presence of motion is detected in at least one of the image blocks.

13. The method of claim 11, further comprising
applying a weight to each respective one of the image blocks, wherein a weight amount applied to each respective image block is determined based on an amount of detected motion associated with the respective image block.

14. A radiation image photographing apparatus for generating a still image from a plurality of projected time-series images obtained in time series, the apparatus comprising:
an image storing unit to store the time-series images;
a difference value calculating unit to calculate a difference value between a value of a pixel of an entire or a part of at least one time-series image and a value of a corresponding pixel of an entire or a part of another time-series image;
a motion detecting unit to detect presence or absence of motion by comparing the difference value calculated by the difference value calculating unit and a threshold value; and
an image synthesizing unit to synthesize the stored time-series images based on a result of the motion detecting so as to generate a synthesized still image.

15. A radiation image photographing apparatus for generating a still image from a plurality of projected time-series images obtained in time series, the apparatus comprising:
a X-ray irradiating unit to irradiate an X-ray towards an object to be examined;
an image storing unit to store images obtained by irradiating the X-ray to pass through the object by the X-ray irradiation unit as the time-series images;
a difference value calculating unit to calculate a difference value between a value of a pixel of an entire or a part of at least one time-series image and a value of a corresponding pixel of an entire or a part of another time-series image;
a motion detecting unit to detect presence or absence of motion by comparing the difference value calculated by the difference value calculating unit and a threshold value;
an image synthesizing unit to synthesize the stored time-series images based on a result of the motion detecting so as to generate a synthesized still image; and
a X-ray irradiation control unit to control the X-ray irradiation unit to stop the irradiation of the X-ray, if motion is detected by the motion detecting unit.

* * * * *